US012774230B2

(12) United States Patent
Cao et al.

(10) Patent No.: US 12,774,230 B2
(45) Date of Patent: Oct. 27, 2026

(54) SYSTEM AND METHOD FOR MONITORING AND ADDING DISINFECTANT IN ANIMAL DRINKING WATER USING OXIDATION-REDUCING POTENTIAL

(71) Applicant: NCH Corporation, Irving, TX (US)

(72) Inventors: Haibo Cao, Flower Mound, TX (US); David F. Vela, Euless, TX (US); Rongxian Liang, Irving, TX (US); Joshua R. Medford, Grand Prairie, TX (US); Chris Zetena, Dallas, TX (US); Anuchit Numsri, Sriracha (TH); Gabriel F.K. Everett, Mansfield, TX (US)

(73) Assignee: NCH Corporation, Irving, TX (US)

(*) Notice: Subject to any disclaimer, the term of this patent is extended or adjusted under 35 U.S.C. 154(b) by 1047 days.

(21) Appl. No.: 17/527,729

(22) Filed: Nov. 16, 2021

(65) Prior Publication Data

US 2022/0153616 A1 May 19, 2022

Related U.S. Application Data

(60) Provisional application No. 63/114,885, filed on Nov. 17, 2020.

(51) Int. Cl.
*C02F 1/76* (2023.01)
*A01N 59/00* (2006.01)
(Continued)

(52) U.S. Cl.
CPC ................ *C02F 1/76* (2013.01); *A01N 59/00* (2013.01); *A01P 1/00* (2021.08); *C02F 1/008* (2013.01);
(Continued)

(58) Field of Classification Search
None
See application file for complete search history.

(56) References Cited

U.S. PATENT DOCUMENTS 4,049,382 A 9/1977 Ross
4,767,511 A 8/1988 Aragon
(Continued)

FOREIGN PATENT DOCUMENTS

WO WO2021247975 12/2021

OTHER PUBLICATIONS

WHO Guidelines for Drinking-Water Quality Fourth Edition 2011 2011 https://www.who.int/publications/i/item/9789241548151, retrieved Jan. 22, 2026.

*Primary Examiner* — Richard C Gurtowski
(74) *Attorney, Agent, or Firm* — Ingrassia Fisher & Lorenz LLP

(57) ABSTRACT

A system and method for monitoring disinfectant levels in non-human animal drinking water using ORP and optionally pH measurements and adding disinfectant or pH adjusting agents as needed. Sensors obtain measurements of the water upstream of a point of consumption and a controller compares measurements to predetermined thresholds, ranges, or previous measurements to determine if the disinfectant and optionally pH levels are within a desired range or above or below a desired minimum or a desired maximum value. A disinfectant dosing system preferably automatically adds disinfectant to the supply line based on the measurement comparison. A flow switch preferably keeps the system from activating disinfectant addition when water in the supply line is static (non-flowing). An alert is preferably triggered when a measurement indicates the disinfectant level is too low or too high or when a volume of disinfectant in the dosing system is below a predetermined volume threshold.

34 Claims, 2 Drawing Sheets

(51) Int. Cl.

| | |
|---|---|
| ***A01P 1/00*** | (2006.01) |
| ***C02F 1/00*** | (2023.01) |
| ***C02F 1/66*** | (2023.01) |
| ***C02F 1/68*** | (2023.01) |
| ***G01N 33/18*** | (2006.01) |
| *C02F 103/20* | (2006.01) |

(52) U.S. Cl.
CPC ................ *C02F 1/66* (2013.01); *C02F 1/686* (2013.01); *G01N 33/18* (2013.01); *C02F 2103/20* (2013.01); *C02F 2209/001* (2013.01); *C02F 2209/04* (2013.01); *C02F 2209/06* (2013.01); *C02F 2209/40* (2013.01); *C02F 2303/04* (2013.01)

(56) References Cited

U.S. PATENT DOCUMENTS

| | | | | |
|---|---|---|---|---|
| 5,422,014 | A | 6/1995 | Allen | |
| 6,372,126 | B1 * | 4/2002 | Reeves | C02F 1/688 210/91 |
| 6,423,234 | B1 | 7/2002 | Martin | |
| 9,858,792 | B2 | 1/2018 | Fernandes | |
| 10,150,680 | B1 | 12/2018 | Kurani | |
| 2005/0139530 | A1 * | 6/2005 | Heiss | C02F 9/00 210/257.2 |
| 2005/0224409 | A1 * | 10/2005 | Harshman | C02F 3/006 210/209 |
| 2010/0183744 | A1 * | 7/2010 | Weissman | C12N 1/12 424/665 |
| 2010/0189805 | A1 * | 7/2010 | Saefkow | C02F 1/4672 204/263 |
| 2011/0011736 | A1 * | 1/2011 | Yost, III | C25B 9/00 204/263 |
| 2013/0284647 | A1 | 10/2013 | Briscoe | |
| 2013/0313204 | A1 * | 11/2013 | Shalon | C02F 1/687 210/744 |
| 2015/0076058 | A1 * | 3/2015 | Brooks | C02F 3/284 210/603 |
| 2018/0009686 | A1 | 1/2018 | Boyle | |
| 2018/0016163 | A1 | 1/2018 | Denvir et al. | |
| 2019/0225521 | A1 | 7/2019 | Heath | |
| 2021/0009453 | A1 | 1/2021 | Boyle et al. | |

* cited by examiner

SYSTEM AND METHOD FOR MONITORING AND ADDING DISINFECTANT IN ANIMAL DRINKING WATER USING OXIDATION-REDUCING POTENTIAL

CROSS-REFERENCE TO RELATED APPLICATION

This application claims the benefit of U.S. Provisional Application Ser. No. 63/114,885 filed on Nov. 17, 2020.

BACKGROUND OF THE INVENTION

1. Field of the Invention

This invention relates to a system and method for monitoring disinfectant levels in non-human animal drinking water and automatically adding disinfectant as needed to maintain a desired minimum level to ensure safety of the drinking water.

2. Description of Related Art

Animal farms draw water from different sources (such as rivers, ponds, or underground) for potable use for animals. These water sources can be contaminated by numerous pollutants, including disease-causing organisms, or pathogens. Pathogens in animal drinking water can lead to serious consequences, including weight loss, reduced productivity, sickness, death, or even transmission of the disease to human beings as the end user. To reduce risk, animal farms apply chemicals (disinfectants) to inactivate pathogens to ensure the drinking water safety.

Currently, animal farms use different types of disinfectants to treat drinking water, including chlorine, chlorine dioxide, ozone, and other disinfectants. The disinfecting capability in the water depends on not only disinfectant level, but also other physical and chemical factors, such as pH, temperature, and water hardness. Many farms only measure and monitor the disinfectant level in the water. This practice masks the real disinfecting capability of the water, which can cause disinfectant under-dose (resulting in an increase in pathogens in the animal drinking water) or over-dose (which is wasteful and can be harmful to the animals or cause the animals to stop drinking or ingest less water than needed). Inconsistency in disinfectant dosing may lead to biological safety issues on the farm.

The most popular water disinfection method is chlorination. Chlorine can be applied in many ways, including chlorine gas ($Cl_2$), sodium hypochlorite (NaClO), or calcium chlorite ($Ca(ClO_2)_2$). When chlorine reacts with water, the reaction forms hypochlorous acid (HClO) and hypochlorite ion ($ClO^-$), both of which play a key role in oxidation and disinfection. The activity of hypochlorous acid as a disinfectant is higher than that of the hypochlorite, being almost 80-100 times more powerful. The pH of the water is an important determinant in the ratio of hypochlorous acid and hypochlorite ions. The proportion of hypochlorous acid decreases from around 100% in a solution with a pH around 6.0 down to almost 0% at pH of around 9.0. The combination of hypochlorous acid and hypochlorite ions is called free chlorine. Free chlorine is widely measured and controlled as the primary parameter to indicate the disinfecting potential of the water. However, the water disinfecting capacity does not depend only on the levels of free chlorine, but also the pH level since it changes the distribution of hypochlorous acid and hypochlorite ions which impacts the disinfecting capacity significantly.

Oxidation-Reduction Potential (ORP) is an electronic measurement, in millivolts (mV), of the oxidizing capability in the water. Oxidizers remove electrons from microbial membranes which compromises the structure and rigidity of the membrane. This destabilizes the microbe, resulting in rapid death via cellular lysis. ORP is a reliable indicator of the real-time disinfecting capability of water. It is known to use ORP sensors in systems designed to control disinfectant or chlorine addition to non-drinking, circulating water systems, such as swimming pools, spas, and cooling towers. For example, U.S. Pat. No. 5,422,014 discloses a system that uses an ORP sensor, pH sensor, and a controller to measure the ORP and pH of a diverted portion of swimming pool water (around 5% of the total water flow circulating through the pool system is sent through a service loop for measurement and injection of chemicals) and inject chlorine and/or an acid to modify the pH based on the measurements. As another example, U.S. Pat. No. 6,423,234 discloses a method of controlling chloramine levels in an indoor swimming pool, both in the pool and in the air, using an ORP sensor and chemical additions, including a coagulating agent to reduce the amount of halogen donor when needed, in order to maintain the ORP reading at between 700 and 850 mv and to maintain the pool at the breakpoint chlorine level (super chlorinated). These systems and methods are unique to swimming pool and recirculating water systems and are not used for drinking water systems.

For drinking water, the World Health Organization has published Guidelines for Drinking-water Quality for human water sources (for drinking, bathing, and food preparation) which indicate an ORP measurement can be used in the operational monitoring of disinfection efficacy. The Guidelines state that it "is possible to define a minimum level of oxidation-reduction potential necessary to ensure effective disinfection [but this] value has to be determined on a case-by-case basis; universal values cannot be recommended." As such, there is no known system or method that can reliably measure disinfectant levels for animal drinking water with integrated control of a disinfectant dosing system. There is a need for a system and method that can utilize (1) a universal parameter to indicate the disinfecting capacity of animal drinking water, and (2) apply an automatic control system to adjust disinfectant dosing and pH in a timely manner to ensure the quality of animal farm drinking water.

SUMMARY OF THE INVENTION

According to one preferred embodiment of the invention, a monitoring system and method uses ORP technology to automatically monitor and control disinfectant levels in animal farm drinking water by adding disinfectant as needed to maintain a desired minimum level of disinfectant in the drinking water to ensure animal drinking water safety. Preferably, the monitoring system comprises a controller and an in-line ORP sensor or probe. The in-line ORP sensor takes readings of the oxidation-reduction potential in the drinking water flowing through a supply line and sends signals to the controller indicating a measurement of the level of disinfectant in the drinking water. Most preferably, the ORP sensor is compatible with different types of disinfectants which have a positive co-relationship with ORP measurement including, without limitation, chlorine, sodium hypochlorite, calcium chlorite, chlorine dioxide, monochloramine, fluorine, bromine, potassium permanganate, iodine, and/or ozone. Most preferably, the measurement is in millivolts. According to another preferred embodiment, the controller converts the millivolt signal into a measurement in different units, such as a concentration of disinfectant.

According to another preferred embodiment, the controller compares the measurement (in millivolts or as converted into other units) to one or more predetermined thresholds or to one or more prior measurements to determine if the measured level of disinfectant is within a desired range, is below the desired range (or below a lower threshold), and/or is above a desired range (or above a high threshold).

According to another preferred embodiment, the monitoring system further comprises a disinfectant dosing system. One preferred embodiment of the disinfectant dosing system comprises a pump that is preferably controlled by the controller to activate the pump to add disinfectant from a container of disinfectant to the drinking water when a measurement or a comparison of a measurement indicates that additional disinfectant is needed. According to another preferred embodiment, the disinfectant dosing system comprises a valve that is controlled by the controller to open and dose to allow disinfectant to feed into the supply line from the container by gravity feed. Most preferably, the disinfectant is in a liquid/solution form that can be pumped or fed by gravity feed from the container, but solid forms with an added dissolution system to form a liquid solution may also be used. Most preferably, the disinfectant in the container is chlorine, sodium hypochlorite, calcium chlorite, chlorine dioxide, monochloramine, fluorine, bromine, potassium permanganate, iodine, and/or ozone.

According to another preferred embodiment, the ORP probe will monitor the ORP level in the animal drinking water and send a signal to the ORP controller. When the ORP value does not reach the desired level, the ORP controller will send a signal to turn on the chemical or disinfectant dosing system to dose more disinfectant into the water to promote an appropriate ORP level. Once the ORP probe detects that the ORP value has reached the desired level, the ORP controller will send a signal to turn off the chemical pumping system to stop the disinfectant dosing According to another preferred embodiment, the monitoring system may comprise a pH adjustment system to monitor and adjust pH in order to optimize the disinfecting capacity of the water. Most preferably, the pH adjustment system comprises an in-line pH sensor/meter/probe that takes pH readings or measurements in the drinking water flowing through a supply line and sends signals to the controller indicating a measurement of the pH level of the drinking water. One preferred embodiment of the pH adjustment system further comprises a pump that is preferably controlled by the controller to activate the pump to add a pH adjusting agent from one or more containers to the drinking water when a pH measurement indicates that the pH should be raised or lowered to achieve optimal disinfection. According to another preferred embodiment, the pH adjustment system comprises a valve that is controlled by the controller to open and close to allow a pH adjusting agent from one or more containers to feed into the supply line from the container(s) by gravity feed. Most preferably, the pH adjusting agent comprise one or more acids in a first container and optionally one or more bases in a second container, in a liquid/solution form that can be pumped or fed by gravity feed from the container(s), but solid forms with an added dissolution system to form a liquid solution may also be used.

According to another preferred embodiment, the monitoring system comprises a flow switch indicating whether water is flowing or static in a supply line. Most preferably, the monitoring system is only active when the flow switch indicates water is flowing through the supply line.

Preferred embodiments of the invention ensure that animal drinking water has the correct ORP level to maintain the correct disinfecting capacity. Preferred embodiments have the advantage of automatic ORP monitoring and addition of disinfectant as needed to animal farm drinking water to maintain the ORP in a reasonable range to ensure proper disinfecting capacity. This invention measures the ORP level in a timely manner and controls the disinfectant dosing automatically, based on the ORP in-line reading. It has not previously been known to use ORP measurements to maintain a disinfectant level in animal drinking water.

BRIEF DESCRIPTION OF THE DRAWINGS

The system of the invention is further described and explained in relation to the following figures wherein.

DESCRIPTION OF PREFERRED EMBODIMENTS

Figure 1:
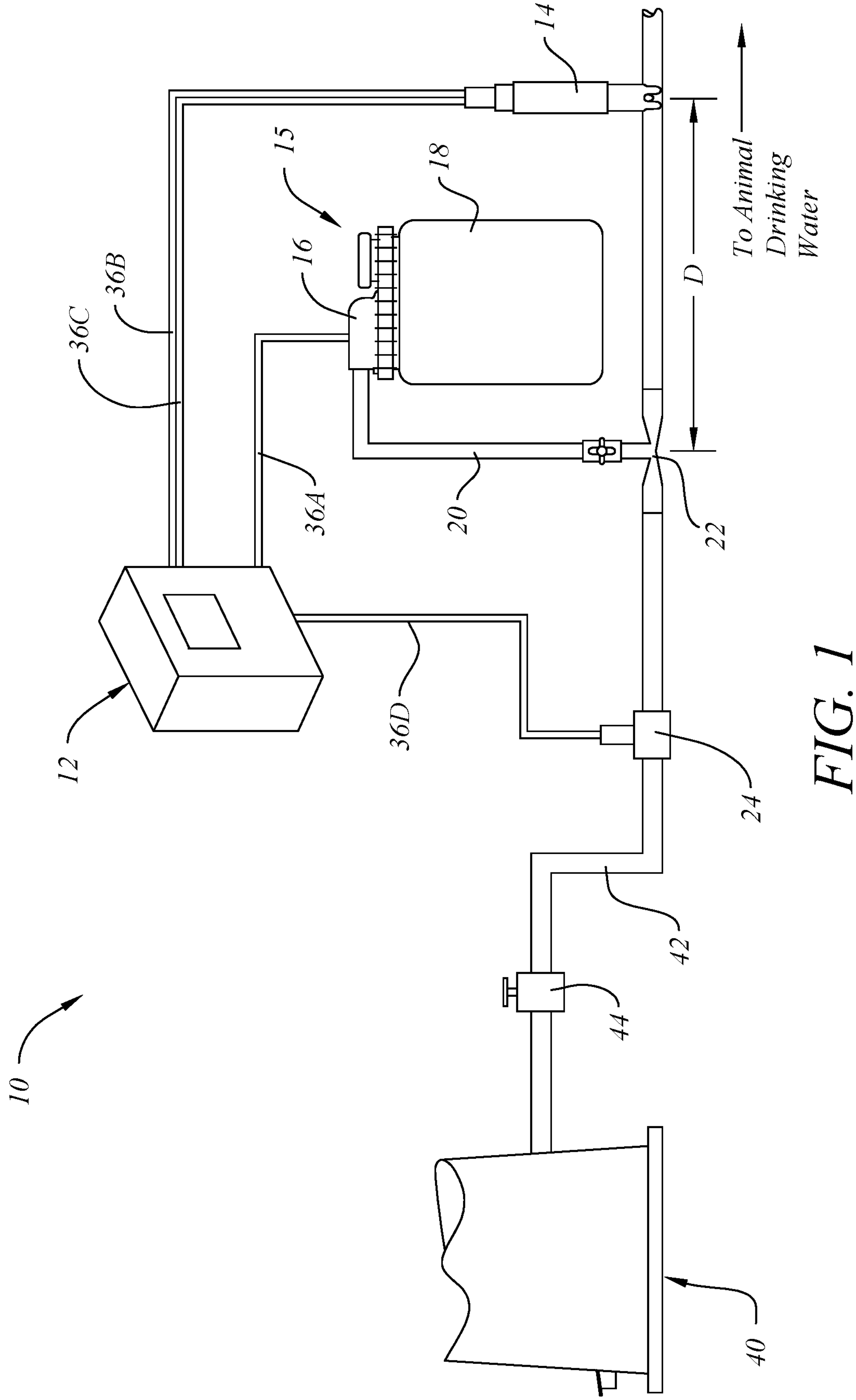
FIG. 1 is a front elevation showing components of an ORP system according to a preferred embodiment of the invention with an animal drinking water system.
Figure 2:
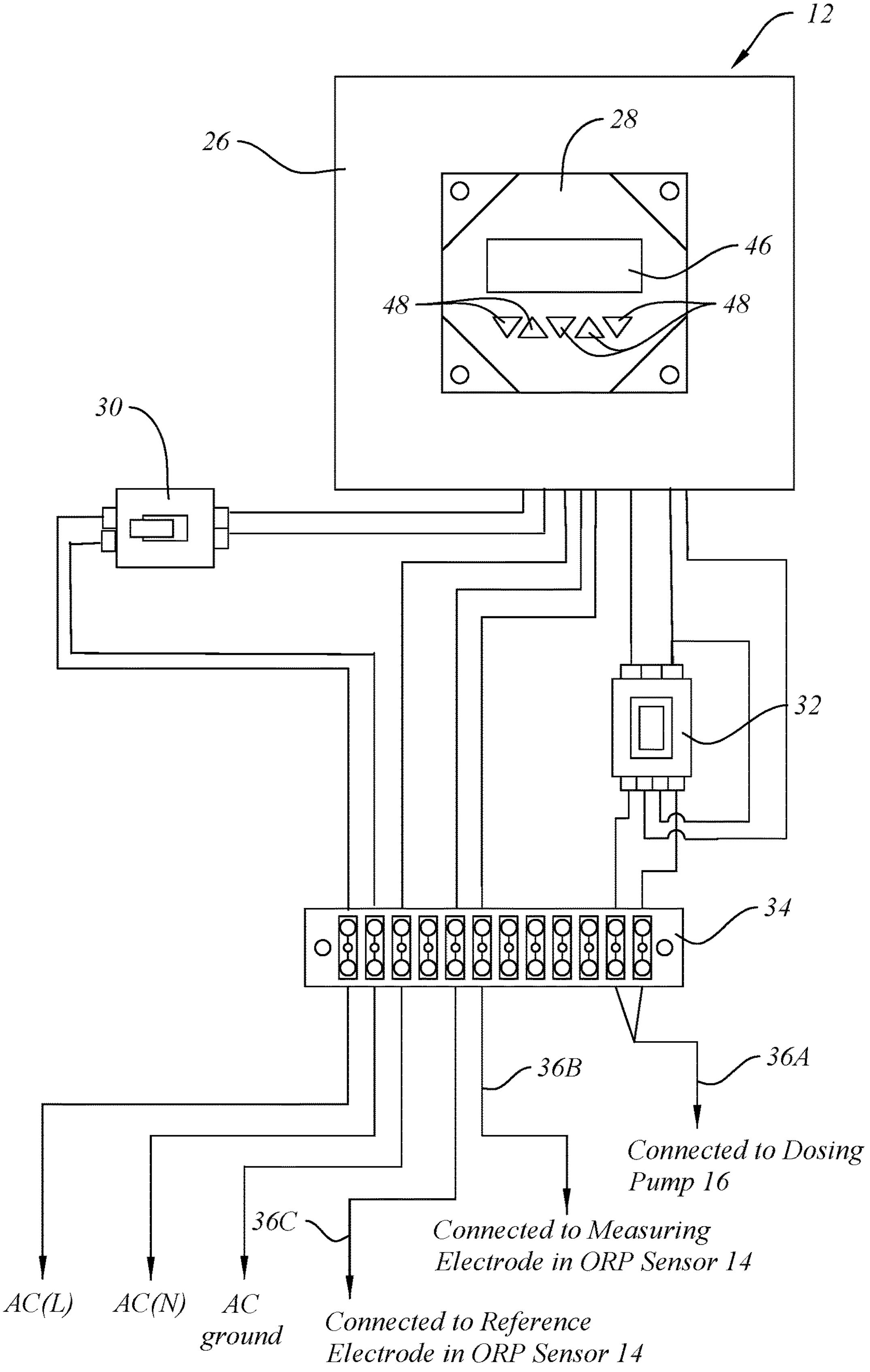
FIG. 2 is a front elevation of certain portions of the ORP system of FIG. 1 shown in more detail.

Referring to FIGS. 1 and 2, an ORP system 10 according to one preferred embodiment of the invention comprises a control system 12, an ORP sensor 14, a disinfectant pumping system 15, and a flow switch 24. The components shown in FIG. 1 are not shown to scale relative to each other. A preferred ORP sensor 14 is one commercially known as Sinomeasure, which is commercially available from Hangzhou Supmea International Trading Co. LTD. A preferred disinfectant pumping system 15 is commercially available as the ProMinent Concept Plus system. Monitoring system 10 is preferably installed at or near an outlet pipeline from water source for the animal drinking water 40, such as a water tower/water tank, a sufficient distance upstream of the trough or other point of consumption for the animals. Most preferably, monitoring system 10 (and specifically injection port or manifold 22) is disposed far enough upstream of the trough or other drinking discharge point that, based on the water flow rate and distance, the disinfectant can contact the water for at least 2 minutes, more preferably at least 10, and in some cases at least 20 minutes (depending on the types of microorganisms in the water source), prior to reaching the point where the animals have access to drink the water to allow sufficient time for disinfection. Most preferably, monitoring system 10 is used to measure disinfectant levels in animal drinking water flowing from a supply source 40 (such as a water tower, but other sources may be used, including directly from rivers, ponds, and municipal water supplies) through a flow line 42, preferably having at least one shut-off or flow control valve 44, to deliver the water to an animal drinking trough and to add disinfectant from container 18 as needed to maintain a disinfectant level in line 42 at a desired level.

Disinfectant dosing system 15 preferably comprises a pump 16 connected in fluid communication with a disinfectant container 18 connected in fluid communication with an injector 22 through a disinfectant discharge line 20. Alternatively, disinfectant dosing system 15 may comprise a valve disposed on container 18 or discharge line 20 to allow disinfectant to be fed by gravity feed from container 18, particularly if container 18 is disposed at an elevated position relative to supply line 42 and discharge line 20 is disposed at or near a bottom of container 18. Discharge line 20 is preferably connected to water supply line 42 at point 22, which may be an injection port, manifold, opening or other access point where disinfectant may be added to the water in line 22 by gravity, dripping, or pumping. As another alternative, point 22 may be directly into the water source, such as a water tower, rather than supply line 42, to allow disinfectant to be added to the water source. Most preferably, ORP sensor 14 is located on supply line 42 at least a distance D of 5 meters; more preferably at least a distance D of 10 meters from point 22 where disinfectant is added to the water.

An optional, but preferred pH adjustment system to monitor and adjust pH in order to optimize the disinfecting capacity of the water may also be used with monitoring system 10. A pH adjustment system could be configured to monitor the pH of the water in supply 42 or in the water source (such as a water tower), similar to the layout of disinfectant dosing system 15 shown in FIG. 1. Most preferably, the pH adjustment system comprises an in-line pH sensor/meter/probe that periodically takes pH readings or measurements in the drinking water flowing through supply line 42 (or at the water source or inlet to supply line 42), one or more containers of pH adjusting agents and a discharge line connected to each container to deliver the pH adjusting agents to the water in supply line 42 (or to the water source). One preferred embodiment of the pH adjustment system further comprises a pump to add a pH adjusting agent from one or more containers to the drinking water. According to another preferred embodiment, the pH adjustment system comprises a valve to allow a pH adjusting agent from one or more containers to feed into the supply line from the container(s) by gravity feed. Preferably, the pH adjusting agent(s) is added at an addition point that is upstream of the disinfectant addition point, and most preferably at least 5-10 meters upstream of the disinfection addition point to allow the pH to be stable prior to the addition of the disinfectant. Most preferably, the pH adjusting agents comprise one or more acids in a first container (or different acids each in one or more separate containers) and optionally one or more bases in a second container (or different bases each in one or more separate containers), in a liquid/solution form that can be pumped or fed by gravity feed from the container(s), but solid forms with an added dissolution system to form a liquid solution may also be used. Preferred acids for pH adjustment agents include, but are not limited to: hydrochloric acid, phosphoric acid, or citric acid or salts of these acids. Alternatively, organic acids such as formic, propionic, lactic, and/or butyric acid or salts of these acids may be used. Preferred bases for pH adjustment agents include, but are not limited to: sodium hydroxide, sodium bicarbonate, and/or potassium carbonate.

Control system 12 preferably comprises a controller 28, a power switch 30, a wire relay 32, and integrated wire board 34, and a plurality of wires or connectors 36 to connect components of control system 12 to each other and to pump 16, ORP sensor 14, and flow switch 24. Wires or connectors 36 may include wire 36A connecting to pump 16, 36B connecting to a measuring electrode in ORP sensor 14, 36C connecting to a reference electrode used with or in ORP sensor 14, and 36D connecting to flow switch 24.

Controller 28 is preferably configured to receive signals (preferably in millivolts) from ORP sensor 14. Most preferably ORP sensor 14 has an internal timing mechanism to automatically take a measurement at periodic intervals, such as every 15-25 seconds, but the ORP sensor may be configured to also receive signals from controller 28 to activate a measurement or to alter the duration of the periodic intervals between measurements. ORP sensor 14 is used to measure the voltage between a measuring electrode (preferably platinum, but other non-oxidizable metal such as gold, palladium, or silver may also be used) and a reference electrode which represents the oxidation reduction potential of the water flowing through line 42. ORP sensor 14 is preferably disposed inline through a port installed on line 42 (not shown) to directly measure the water flowing through line 42. As an alternative, a portion of water may be diverted from line 42 to a sub-circuit into which ORP sensor 14 is installed with the diverted water being reintroduced into line 42 after measuring.

Controller 28 may optionally be configured to convert the signal from ORP sensor 14 into an ORP measurement using a different value conversion or scale, such as converting a millivolt signal from sensor 14 into a concentration of chlorine in line 42, if desired. Controller 28 is further configured to compare one or more ORP measurements (either as a raw signal or a converted measurement), most preferably each ORP measurement, to a predetermined threshold or range or to one or more prior ORP measurements. Most preferably, ORP system 10 has a lower predetermined threshold or a lower alarm ORP point and a higher predetermined threshold or higher alarm ORP point. Lower alarm ORP point is the minimum ORP level in the water to ensure sufficient disinfecting capacity. Most preferably, at a pH of around 7, the lower threshold is around 580 my to 720 my, more preferably 600 my to 700 mv, and most preferably 625 my to 675 mv or around 0.2 to 4 ppm, more preferably 0.25 to 3 ppm, and most preferably 0.6 to 1.8 ppm of chlorine (if converted to a chlorine concentration). The higher alarm ORP point is the maximum ORP level in the water to ensure the ORP level is not too high to have adverse effects on animal health. Most preferably, the higher threshold is around 825 mv to 875 mv, more preferably 835 mv to 865 mv, and most preferably 850 mv to 860 mv or around 2 to 10 ppm, more preferably 3 to 7 ppm, and most preferably 5 to 6 ppm of chlorine (if converted to a chlorine concentration).

If the comparison of an ORP measurement indicates that a level of disinfectant in line 42 is too low, controller 28 is further configured to send a signal to disinfectant dosing system 15 to allow disinfectant to be added to the water at point 22. Preferably, controller 28 sends a signal to pump 16 to activate pump 16 (or to a valve to open a valve for gravity feed of disinfectant) to deliver an amount of disinfectant stored in container 18 to the water flow line 42 (or to the water source) through an injector 22. Preferably, controller 28 activates pump 16 (or keeps valve open) until a comparison of ORP measurement indicates the disinfection level is above the lower threshold, more preferably until a comparison indicates the disinfection level has reached an intermediate level that is around 5-10% lower than the higher threshold. Alternatively, controller 28 may activate pump 16 (or keep a valve open) until the next comparison that meets or exceeds the higher threshold. As an additional alternative, controller 28 may be configured to determine an amount of disinfectant needed to bring the level up to a desired level above the lower threshold based on the flow rate through line 42 and the ORP measurement that triggers disinfectant addition and to activate pump 16 (or open a valve) for an amount of time based on pumping rate (or gravity feed rate)

necessary to deliver the determined amount of disinfectant to achieve the desired ORP measurement level. Pump 16 (or a valve) may also be activated by controller 28 for a predetermined amount of time, such as using a timer. Although it is preferred that controller 28 automatically control the addition of disinfectant through disinfectant dosing system 15, controller may also be configured to send an alert to a user that disinfectant needs to be added or when sufficient disinfectant has been added so that the user can manually operate disinfectant dosing system 15.

Controller 28 is preferably configured to receive signals from a pH sensor in an optional pH adjustment system and to convert the signal to a pH reading if needed. Most preferably pH sensor has an internal timing mechanism to automatically take a measurement at periodic intervals, such as every 15-25 seconds, but the pH sensor may be configured to also receive signals from controller 28 to activate a measurement or to alter the duration of the periodic intervals between measurements. A pH sensor is used to measure the pH of the water flowing through line 42 or in the water source (such as a water tower). A pH sensor is preferably disposed inline through a port installed on line 42 to directly measure the water flowing through line 42. As an alternative, a portion of water may be diverted from line 42 to a sub-circuit into which a pH sensor is installed with the diverted water being reintroduced into line 42 after measuring.

Controller 28 can be further configured to compare one or more pH measurements (either as a raw signal or a converted measurement), most preferably each pH measurement, to a predetermined acceptable threshold or range based on the specific disinfectant use, or to one or more prior pH measurements. Most preferably, system 10 has a lower predetermined pH threshold or a lower alarm pH point and a higher predetermined pH threshold or higher alarm pH point. Lower alarm pH point is preferably the minimum desired pH level in the water to aid in optimizing disinfecting capacity without harming the animals or causing damage to the components of system 10. Upper alarm pH point is preferably the maximum desired pH level in the water to aid in optimizing disinfecting capacity without harming the animals. The optimal pH and the lower and upper pH thresholds are dependent on the preferred disinfectant and are predetermined and programmed into the controller as appropriate. Preferred ranges include chlorine derivatives (chlorine, sodium hypochlorite, calcium chlorite) at an optimal pH of 5 to 7.5, monochloramine at an optimal pH of 7 to 9, potassium permanganate at an optimal pH of 6 to 7, and bromine at an optimal pH of 6 to 8.

If the comparison of a pH measurement indicates that a pH level of the water in line 42 is too low, controller 28 is further configured to send a signal to pH adjustment system to allow a pH adjusting agent (a base if the pH is too low) to be added to the water at a pH adjustment injection or addition point, preferably near point 22 and more preferably upstream of point 22. Preferably, controller 28 sends a signal to a pump to activate the pump (or to a valve to open a valve for gravity feed of pH adjusting agent) to deliver an amount of pH adjusting agent stored in a container to the water flow line 42 (or to the water source) through an injector (like injector 22). Preferably, controller 28 activates a pump (or keeps valve open) until a comparison of pH measurement indicates the pH level is above the lower pH threshold, more preferably until a comparison indicates the pH level has reached an intermediate level between the low pH threshold and high pH threshold, such as between 5.5 to 7.5, more preferably between 6 to 7. Alternatively, controller 28 may activate a pump (or keep a valve open) until the next comparison that meets or exceeds the higher pH threshold. As an additional alternative, controller 28 may be configured to determine an amount of pH adjusting agent needed to bring the level up to a desired level above the lower threshold based on the flow rate through line 42 and the pH measurement that triggers pH adjusting agent addition and to activate a pump (or open a valve) for an amount of time based on pumping rate (or gravity feed rate) necessary to deliver the determined amount of pH adjusting agent to achieve the desired pH measurement level. A pump (or a valve) may also be activated by controller 28 for a predetermined amount of time, such as using a timer, to deliver pH adjusting agent. Although it is preferred that controller 28 automatically control the addition of pH adjusting agents through pH adjustment system, controller may also be configured to send an alert to a user that a pH adjusting agent needs to be added or when sufficient pH adjusting agent has been added so that the user can manually operate the pH adjustment system.

Controller 28 may also be configured to trigger an alert, such as an audible or visual alarm or to send a signal or message to a user, to indicate that an ORP or pH measurement is above or below one of the thresholds or range of thresholds; to store ORP or pH data and send or allow transfer of historic data to another device, such as a computer, tablet, or cell phone. Control system 12 also preferably comprises a user interface, preferably with a display screen 46 and one or more buttons 48 to allow user inputs. Most preferably, a user may view information regarding ORP system 10 on a display screen, such as ORP measurements, pH measurement, comparisons, activation of pump 16, and/or disinfectant dosage amounts added using pump 16, pH adjusting agent dosage amounts, and input data or instructions into system 10 using one or more buttons or a touch screen, such as instructions to recall information to be displayed, to change one of the thresholds, to manually activate pump or manually stop pump, and/or to turn system 10 on or off (which may also be done with power switch 30).

Controller 28 is preferably configured to receive a signal from flow switch 24 indicating whether water is flowing through drinking water flow line 42 (dynamic flow) or not flowing (static flow). If no water is flowing through line 42 (static water flow detected), then the ORP system 10 is preferably in a "pending" or inactive state. This will ensure the ORP system will not run idle when no water is flowing in the pipeline, such as during overnight hours when water is not typically consumed by farm animals. If dynamic water flow is detected, then the ORP system 10 will preferably be in an "active" state. When in a pending or inactive state, ORP system 10 preferably does not take any readings with sensor 14, or optionally convert signals from sensor 14 to measurements, or make any comparisons. When in an active state, a signal is sent from ORP sensor 14 to controller 28 preferably every 15-25 seconds.

Controller 28 may optionally be configured to alert a user of a low level of disinfectant in container 18 by sending a signal or message to a user or trigger an audible or visual alarm when a level of disinfectant in container 18 reaches a predetermined threshold or predetermined low level so that a user can be alerted that container 18 needs refilling or replacement. Disinfectant dosing system 15 may further comprise a level sensor disposed in or on container 18 and configured to send signals to controller 28 indicating the level in container 18. Alternatively, controller 28 may be configured to calculate and track the amount of disinfectant injected into line 42 and to compare it to an initial volume of disinfectant in container 18 to calculate a level of disinfectant remaining in container 18. Controller 28 may be configured to initiate a low level alert when the remaining volume of disinfectant in container 18 is below a predetermined threshold, such as 10% or 5% volume remaining to indicate the container is near empty (or actually empty, if desired) so that it may be refilled or replaced. According to yet another preferred embodiment, controller 28 also tracks inventory of replacement containers 18 or a replenishment volume of disinfectant to be added to refill container 18 and can provide an alert or automatically send a replacement order to replenish inventory of disinfectant when the supply of disinfectant at the treatment location is low. Controller 28 may similarly be configured to calculate and track amounts of pH adjusting agents used and inventory and to send alerts or replenishment orders.

Monitoring system 10 may also be used with a water supply system that has a preexisting disinfectant dosing or addition system, in which case monitoring system 10 does not comprise a disinfectant dosing system. In that case, controller 28 may be configured to send a signal to the external/preexisting dosing or addition system when a comparison of measurements indicates additional disinfectant is needed or to send an alert to a user to make the addition manually or using a separate control system for the external/preexisting disinfectant dosing or addition system.

Enclosure or housing 26 preferably protects controller 28 from incidental contact by untrained personnel, water, fire, and foreign objects. Enclosure or housing 26 also provides a certain degree of fire protection and water resistance. Most preferably, enclosure or housing 26 is waterproof to extend equipment life and decrease maintenance. Enclosure or housing 26 and components of the disinfectant dosing system are preferably disposed in a semi-sheltered environment, preferably under an overhead cover or roof. Enclosure or housing 26 is preferably compact in size. An exemplary size according to one preferred embodiment is around 400 mm×200 mm×570 mm.

Power switch 30 provides an electrical connection from a voltage source/ground to a load. It saves power across multiple voltage rails and protects subsystems from damage. Wire relay 32 preferably controls a high power/voltage circuit for pump 16 with a lower power circuit from the ORP controller 28. Galvanic isolation is desirable, but not required. Integrated wire board 34 integrates several components in system 10 which are inseparably associated and electrically interconnected. The wire board also aids the assembly of the whole system by coordinating the wire connections between several elements. Components 30, 32, and 34 are shown outside of enclosure 26 in FIG. 2 for purposes of visibility, but are preferably disposed inside enclosure 26 in use.

According to one preferred embodiment, a method of monitoring a level of disinfectant in animal drinking water comprises: (1) periodically obtaining an ORP measurement (and optionally a pH measurement), of water flowing as it flows through a supply line from a water source to a point of animal consumption using an ORP sensor (and optionally a pH sensor); (2) comparing one or more of the ORP (and/or optionally pH) measurements to a predetermined low value ORP (or pH) threshold, a predetermined high value ORP (or pH) threshold, a predetermined acceptable ORP (or pH) range, one or more prior ORP (or pH) measurements, or a combination thereof; and (3) adding disinfectant (or a pH adjusting agent) from one or more containers having an initial volume of disinfectant (or one or more pH adjusting agents) to an addition point in the supply line if the ORP (or pH) measurement is below the predetermined low value ORP (or pH) threshold or below the predetermined acceptable ORP (or pH) range. According to other preferred embodiments, the method further comprises one or more of the following steps: (4) deactivating the pump or closing the valve to stop adding disinfectant and/or pH adjusting agent once a new ORP or pH measurement is above the high value predetermined threshold or is within the predetermined acceptable range for ORP or pH, respectively; (5) determining whether water is flowing through the supply line or is static and carrying out the comparing step only when water is flowing through the supply line; (6) triggering a first alert when the ORP or pH measurement is below the predetermined low value threshold, above the predetermined high value threshold, or outside the predetermined acceptable range for the ORP or pH measurement, respectively; (7) determining a remaining volume of disinfectant or pH adjusting agent in the one or more containers, comparing the remaining volume to a predetermined volume level, and triggering a second alert when the remaining volume is below the predetermined volume level for the disinfectant or pH adjusting agent, respectively. According to another preferred embodiment, the adding step(s) comprises activating a pump to pump disinfectant or pH adjusting agent from the one or more containers through a discharge line to the addition point or opening a valve on the one or more containers or on one or more discharge lines connected to the container(s) to allow disinfectant or pH adjusting agent to flow by gravity feed from the container to the addition point. Most preferably, the methods of the invention are carried out using a preferred monitoring system, such as system 10.

References herein to animals include all animals raised for agricultural purposes, or as a source of foods for humans, such as livestock and aquatic species, but specifically exclude humans. References herein to drinking water are to drinking water for consumption by animals, not drinking water for human consumption.

References herein to measurements, reading, calculating or measuring a value, parameter, or property and the like are intended to include any form of direct measurement, converting data or a signal, making a calculation based on one or more data points or signals, or otherwise comparing, interpreting, correlating, or manipulating one or more data points or signals unless specifically excluded. Unless specifically excluded, any preferred features and optional components of system and/or method steps described herein may be used with any other embodiment, even if not specifically described herein with that particular embodiment. All dimensions, sizes, numerical rating, ratio, or percentages indicated herein as a range include each individual amount or ratio within those ranges and any and all subset combinations within ranges, including subsets that overlap from one preferred range to a more preferred range. Those of ordinary skill in the art will also appreciate upon reading this specification, including the examples contained herein, that modifications and alterations to the preferred embodiments of may be made within the scope of the invention and it is intended that the scope of the invention disclosed herein be limited only by the broadest interpretation of the appended claims to which the inventor is legally entitled.

What is claimed:

1. A method of monitoring a level of disinfectant in animal drinking water, the method comprising:

periodically receiving ORP signals from an ORP sensor using a controller, wherein each of the ORP signals indicates a measurement of a chlorine level in the animal drinking water, and wherein the ORP sensor is disposed at a first measurement point and in contact with the animal drinking water as it flows through a supply line from a water source to a point of animal consumption;

comparing the measurement of the chlorine level to a first predetermined low value threshold, a first predetermined high value threshold, a first predetermined acceptable range, the measurement of the chlorine level indicated by one or more previous of the ORP signals, or a combination thereof using the controller; and sending a disinfectant signal from the controller to a disinfectant dosing system comprising a first container of a disinfectant in fluid communication with the supply line, the disinfectant signal being to add or to stop adding the disinfectant to the animal drinking water flowing through the supply line at a first addition point in the supply line based on the comparing the measurement of the chlorine level step;

wherein the first addition point is disposed upstream of the first measurement point;

wherein the first container has an initial volume of the disinfectant and wherein the disinfectant comprises chlorine from chlorine gas, sodium hypochlorite, or calcium chlorite; and wherein the animal drinking water flows directly through the supply line from the water source to the point of animal consumption, passing through the first addition point one time and passing through the first measurement point one time regardless of the controller sending the disinfectant signal to the disinfectant dosing system to add or to stop adding the disinfectant at the first addition point based on the comparing the measurement of the chlorine level step.

2. The method of claim 1 wherein when the disinfectant signal is to add disinfectant, the method further comprises: (1) activating a pump to pump the disinfectant from the first container through a discharge line to the first addition point or (2) opening a valve on the first container or on the discharge line to allow the disinfectant to flow by gravity feed from the first container to the first addition point.

3. The method of claim 2 wherein when the disinfectant signal is to stop adding disinfectant, the method further comprises: deactivating the pump or closing the valve to stop adding the disinfectant.

4. The method of claim 1 further comprising determining whether the animal drinking water is flowing through the supply line or is static and wherein the comparing the measurement of the chlorine level step only occurs when the animal drinking water is flowing through the supply line.

5. The method of claim 1 wherein the first addition point is disposed at least 10 meters upstream from the ORP sensor.

6. The method of claim 1 further comprising periodically receiving pH signals from an in-line pH sensor using the controller, wherein each of the pH signals indicates a pH measurement in the animal drinking water as it flows through the supply line;

comparing the pH measurements to a second predetermined low value threshold, a second predetermined high value threshold, a second predetermined acceptable range, the pH measurement indicated by one or more previous pH signals, or a combination thereof; and sending a pH adjustment signal from the controller to a pH adjusting system comprising (1) a second container of a pH lowering agent in fluid communication with the supply line at a second addition point upstream of the first addition point, (2) a third container of a pH raising agent in fluid communication with the supply line at a third addition point upstream of the first addition point, wherein the third addition point may be the same as the second addition point or may be separate from the second addition point;

wherein the pH adjustment signal is to add or to stop adding one of the pH lowering agent or the pH raising agents to the animal drinking water flowing through the supply line based on the comparing the pH measurement step.

7. The method of claim 6 wherein the pH adjustment signal is to add (1) the pH lowering agent when the pH measurement in the comparing the pH measurement step is above the second predetermined acceptable range or above the second predetermined high value threshold and (2) the pH raising agent when the pH measurement in the comparing the pH measurement step is below the second predetermined low value threshold or is below the second predetermined acceptable range.

8. The method of claim 5 further comprising triggering a first alert when the measurement of the chlorine level is below the first predetermined low value threshold, above the first predetermined high value threshold, or outside the first predetermined acceptable range.

9. The method of claim 8 further comprising determining a remaining volume of the disinfectant in the first container, comparing the remaining volume to a first predetermined volume level, and triggering a second alert when the remaining volume is below the first predetermined volume level.

10. A system for monitoring disinfectant level in animal drinking water, the system comprising:

an ORP sensor disposed at a first measurement point and in contact with the animal drinking water as it flows through a supply line from a water source to a point of animal consumption;

a disinfectant dosing system comprising a first container of a disinfectant in fluid communication with the supply line to add the disinfectant to the animal drinking water in the supply line at a first addition point disposed upstream of the first measurement point, wherein the disinfectant comprises chlorine from chlorine gas, sodium hypochlorite, or calcium chlorite; and a controller configured to (1) receive an ORP signal from the ORP sensor indicating a measurement of a chlorine level in the animal drinking water at the first measurement point, (2) make a comparison of the measurement of the chlorine level to a first predetermined low value threshold, a first predetermined high value threshold, a first predetermined acceptable range, one or more prior measurements of the chlorine level, or a combination thereof, and (3) send a disinfectant signal to the disinfectant dosing system to add the disinfectant at the first addition point or to stop adding the disinfectant at the first addition point based on the comparison;

wherein the animal drinking water flows directly through the supply line from the water source to the point of animal consumption, passing through the first addition point one time and passing through the first measurement point one time regardless of the controller sending a signal to the disinfectant dosing system to add the disinfectant at the first addition point or to stop adding the disinfectant at the first addition point based on the comparison.

11. The system of claim 10 wherein the controller sends the disinfectant signal to add the disinfectant when the measurement of the chlorine level is below or above the first predetermined acceptable range, and wherein the first predetermined acceptable range is between 1.8 and 5 ppm.

12. The system of claim 11 wherein ORP sensor is the only sensor, meter, or probe in the system to measure the chlorine level in the animal drinking water.

13. The system of claim 11 wherein the disinfectant dosing system further comprises a pump to pump the disinfectant from the first container to the supply line and wherein the controller is configured to send the disinfectant signal to activate or deactivate the pump to add or stop adding the disinfectant and wherein the ORP sensor disposed at the first measurement point is the only ORP sensor in the system.

14. The system of claim 11 wherein the disinfectant dosing system further comprises a valve to allow the disinfectant from the first container to feed into the supply line by gravity feed and wherein the controller is configured to send the disinfectant signal to open or close the valve to add or stop adding the disinfectant and wherein the system consists of a single ORP sensor and the single ORP sensor is the ORP sensor disposed at the first measurement point.

15. The system of claim 11 further comprising a flow switch and wherein the controller is further configured to receive a flow signal from the flow switch indicating whether animal drinking water is flowing through the supply line or is static and to make the comparison only when the animal drinking water is flowing.

16. The system of claim 10 wherein the first addition point is disposed at least 10 meters upstream of the ORP sensor.

17. The system of claim 11 further comprising a pH adjusting system comprising an in-line pH sensor disposed at a second measurement point and in contact with the animal drinking water as it flows through the supply line from the water source to the point of animal consumption;

a second container of a pH lowering agent in fluid communication with the supply line to add the pH lowering agent to the animal drinking water at a second addition point upstream of the first addition point;

a third container of a pH raising agent in fluid communication with the supply line to add the pH raising agent to the animal drinking water at a third addition point upstream of the first addition point, wherein the third addition point may be the same as the second addition point or may be separate from the second addition point; and wherein the controller is further configured to (1) receive a pH signal from the in-line pH sensor indicating a pH measurement of the animal drinking water, (2) make a comparison of the pH measurement to a second predetermined low value threshold, a second predetermined high value threshold, a second predetermined acceptable range, one or more prior pH measurements, or a combination thereof; and (3) send a pH agent signal to the pH adjusting system to add the pH lowering agent or the pH raising agent or to stop adding the pH lowering agent or the pH raising agent based on the comparison.

18. The system of claim 16 wherein the first addition point is disposed sufficiently upstream of the point of animal consumption to allow the animal drinking water to be in the supply line between the first addition point and the point of animal consumption for 2-10 minutes.

19. The system of claim 11 wherein the controller is further configured to trigger an alert when the comparison is outside the first predetermined acceptable range and wherein the first addition point is disposed sufficiently upstream of the point of animal consumption to allow the animal drinking water to be in the supply line between the first addition point and the point of animal consumption for 2-10 minutes.

20. The system of claim 11 wherein the controller is further configured to trigger an alert when an amount of disinfectant remaining in the first container is below a first predetermined volume level.

21. The system of claim 17 wherein the second addition point and the third addition point are upstream of the first addition point by at least 5 meters.

22. The system of claim 21 wherein the disinfectant comprises chlorine;

wherein the controller is configured to make the comparison of the measurement of the disinfectant level to the first predetermined low value threshold and the first predetermined high value threshold;

wherein the first predetermined low value threshold is 42 ppm or less of chlorine;

wherein the first predetermined high value threshold is between 10 ppm of chlorine; and wherein the controller is further configured to send the disinfectant signal to add the disinfectant until the measurement of the chlorine level is 5-10% below the first predetermined high value threshold.

23. The system of claim 10 wherein the disinfectant comprises chlorine;

wherein the controller is configured to make the comparison of the measurement of the disinfectant level to the first predetermined low value threshold and the first predetermined high value threshold;

wherein the first predetermined low value threshold is 2 ppm or less of chlorine;

wherein the first predetermined high value threshold is between 10 ppm of chlorine; and wherein the controller is further configured to send the disinfectant signal to add the disinfectant until the measurement of the chlorine level is 5-10% below the first predetermined high value threshold.

24. The system of claim 23 wherein the first addition point is disposed at least 10 meters upstream of the ORP sensor.

25. The system of claim 10 further comprising a pH adjusting system comprising an in-line pH sensor disposed at a second measurement point and in contact with the animal drinking water as it flows through the supply line from the water source to the point of animal consumption;

a second container of a pH lowering agent in fluid communication with the supply line to add the pH lowering agent to the animal drinking water at a second addition point upstream of the first addition point;

a third container of a pH raising agent in fluid communication with the supply line to add the pH raising agent to the animal drinking water at a third addition point upstream of the first addition point, wherein the third addition point may be the same as the second addition point or may be separate from the second addition point; and wherein the controller is further configured to (1) receive a pH signal from the in-line pH sensor indicating a pH measurement of the animal drinking water, (2) make a comparison of the pH measurement to a second predetermined low value threshold, a second predetermined high value threshold, a second predetermined acceptable range, one or more prior pH measurements, or a combination thereof; and (3) send a pH agent signal to the pH adjusting system to add the pH lowering agent or the pH raising agent or to stop adding the pH lowering agent or the pH raising agent based on the comparison.

26. The system of claim 25 wherein the first addition point is disposed sufficiently upstream of the point of animal consumption to allow the animal drinking water to be in the supply line between the first addition point and the point of animal consumption for 2-10 minutes.

27. The system of claim 26 wherein the second addition point and the third addition point are upstream of the first addition point by at least 5 meters; and wherein the first addition point is upstream of the first measurement point by at least 10 meters.

28. The system of claim 26 wherein the system consists of a single ORP sensor and the single ORP sensor is the ORP sensor disposed at the first measurement point.

29. The system of claim 27 wherein the system consists of a single ORP sensor and the single ORP sensor is the ORP sensor disposed at the first measurement point.

30. The system of claim 29 wherein the system consists of a single addition point for the disinfectant into the supply line and the single addition point is the first addition point.

31. The system of claim 10 wherein the first addition point is disposed sufficiently upstream of the point of animal consumption to allow the animal drinking water to be in the supply line between the first addition point and the point of animal consumption for 2-10 minutes.

32. The system of claim 31 wherein the system consists of a single ORP sensor and the single ORP sensor is the ORP sensor disposed at the first measurement point.

33. A system for monitoring disinfectant level in animal drinking water, the system comprising:

a chlorine level sensor, the chlorine level sensor consisting of an ORP sensor disposed at a first measurement point and in contact with the animal drinking water as it flows through a supply line from a water source to a point of animal consumption;

a disinfectant dosing system comprising a first container of a disinfectant in fluid communication with the supply line to add the disinfectant to the animal drinking water in the supply line at a first addition point disposed upstream of the first measurement point, wherein the disinfectant comprises chlorine from chlorine gas, sodium hypochlorite, or calcium chlorite; and a controller configured to (1) receive an ORP signal from the ORP sensor indicating a measurement of a chlorine level in the animal drinking water at the first measurement point, (2) make a comparison of the measurement of the chlorine level to a first predetermined low value threshold, a first predetermined high value threshold, a first predetermined acceptable range, one or more prior measurements of disinfectant level, or a combination thereof, and (3) send a disinfectant signal to the disinfectant dosing system to add the disinfectant at the first addition point or to stop adding the disinfectant at the first addition point based on the comparison;

wherein the animal drinking water flows directly through the supply line from the water source to the point of animal consumption, passing through the first addition point one time and passing through the first measurement point one time.

34. The system of claim 33 further comprising a pH adjusting system comprising an in-line pH sensor disposed at a second measurement point and in contact with the animal drinking water as it flows through the supply line from the water source to the point of animal consumption;

a second container of a pH lowering agent in fluid communication with the supply line to add the pH lowering agent to the animal drinking water at a second addition point upstream of the first addition point by at least 5 meters;

a third container of a pH raising agent in fluid communication with the supply line to add the pH raising agent to the animal drinking water at a third addition point upstream of the first addition point by at least 5 meters, wherein the third addition point may be the same as the second addition point or may be separate from the second addition point;

wherein the controller is further configured to (1) receive a pH signal from the in-line pH sensor indicating a pH measurement of the animal drinking water flowing through the supply line, (2) make a comparison of the pH measurement to a second predetermined low value threshold, a second predetermined high value threshold, a second predetermined acceptable range, one or more prior pH measurements, or a combination thereof; and (3) send a pH agent signal to the pH adjusting system to add the pH lowering agent or the pH raising agent or to stop adding the pH lowering agent or the pH raising agent based on the comparison;

wherein the first addition point is disposed sufficiently upstream of the point of animal consumption to allow the animal drinking water to be in the supply line between the first addition point and the point of animal consumption for 2-10 minutes; and wherein the first addition point is upstream of the first measurement point by at least 10 meters.

* * * * *